United States Patent [19]

Mikkelsen

[11] Patent Number: Plant 5,532

[45] Date of Patent: Aug. 13, 1985

[54] BEGONIA PLANT NAMED HILDA

[75] Inventor: James C. Mikkelsen, Ashtabula, Ohio

[73] Assignee: Mikkelsens, Inc., Ashtabula, Ohio

[21] Appl. No.: 547,671

[22] Filed: Nov. 1, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of begonia plant named Hilda characterized by its deep red flower color; occasional pistillated flowers; ease of propagation; compact, upright growth habit, and by its floriferousness.

1 Drawing Figure

1

The present invention relates to a new and distinctive cultivar of begonia plant, botanically known as *hiemalis begonia, Fotsch,* and known by the cultivar name Hilda.

The new cultivar Hilda is a mutation of Connie, disclosed in pending application Serial No. 420,500 of Erland V. Schelbeck, and was observed in a group of 10 cm. flowering plants. These plants were propagated from the parent cultivar by tissue culture techniques, and Hilda was identified as CON-82-6. Asexual reproduction by stem and leaf cuttings has reproduced the unique features of the new cultivar through successive propagations.

The following characteristics distinguish the new begonia from both its parent and other begonias commercially known and used in the floriculture industry:

1. In comparison to Connie, which has rose-red flower color, Hilda has deep red flower color.

2. Hilda, has an occasional pistillated flower, whereas Connie very seldom shows a tendency to have single or open type flowers.

3. In all other morphological respects, Connie and Hilda very closely resemble each other.

4. In comparison to Ellen, disclosed in pending application Ser. No. 506,213 of Erland V. Schelbeck, Hilda has smaller, less double flowers, smaller and darker foliage, and is less prone to mildew.

5. In comparison to Dorthe, disclosed in pending application Ser. No. 420,421 of Erland V. Schelbeck, Hilda does not have red pigmented foliage, with the foliage of Hilda also being more serrated at the edges; flower color is dark red compared to dark orange-red flowers of Dorthe; growth of Hilda is stronger than Dorthe so that the pedicels support the flowers in a more upright position.

The accompanying colored photograph taken in June, 1983 illustrates in perspective the overall appearance of Hilda, showing the colors as true as it is reasonably possible to obtain in a colored reproduction of this type, especially for red.

The following is a detailed description of my new begonia cultivar based on plants produced under commercial practices in the greenhouses of Mikkelsens, Inc., Ashtabula, Ohio, grown in 10 cm. pots and leaf cutting propagation. Color references are made to The Royal Horticultural Society Colour Chart except where general color terms of ordinary dictionary significance are used. Changes in light, temperatures and nutrition may alter visual colorations of foliage and flowers.

2

Parentage:

Mutation of Connie, disclosed in pending application Ser. No. 420,500.

Propagation:

(A) *Type cutting.*—Leaf cuttings.

(B) *Time to root.*—15 days at 21° C. summer, 24 says at 21° C. winter.

(C) *Rooting habit.*—Rooting is quite uniform, dendritic and fibrous.

(D) *Time for shoot development.*—Total time from sticking the leaf cutting to adventitious shoots 5–6 cm. in length is 65 days in summer to 80 days in winter.

Plant description:

(A) *Form.*—Compact, rounded, close internoded, vigorous, self supporting, herbaceous.

(B) *Habit of growth.*—Rapid, upright, high degree of self-branching.

(C) *Foliage.*—Leaves simple, alternate, borne on vigorous petioles up to 5 mm. in diameter. (1) Size: Average size is 9–10 cm. If plant develops with fewer shoots than illustrated, leaves may be 10–12 cm.; conversely only 5–6 cm. (2) Shape: Ovate to nearly orbicular with overlapping lobes. (3) Texture: Leaf is firm to crisp, top side glabrous, underside rugose. (4) Margin: Highly serrated to crenate. (5) Color: Young foliage, top side, yellow green 147A plus red infusion; under side, yellow green 147C slight reddening; mature foliage top side, near green 147A to 137A, under side, yellow green 148BC. (6) Venation: Palmate.

Flowering description:

(A) *Flowering habits.*—Flowering in racemes with inflorescence having up to 10–12 flowers in bloom at same time, as illustrated. Flowering continues more or less indefinitely.

(B) *Natural flowering season.*—Will flower in all seasons, including summer, without controlling day length. More uniform and abundant flowering does occur with increased maturity of plant and reducing day length to 12 hours.

(C) *Flower bud description.*—Flat and nearly circular; buds begin to open when approximately 2.5 cm. in diameter.

(D) *Flowers born.*—On sturdy pedicels within the form of the raceme.

(E) *Quantity.*—Dependent on the number of shoots that are available for flowering. Plant illustrated in 10 cm. pot has approximately 30 flowers in addition to unopened buds; cultivar considered highly floriferous.

(F) *Tepals.*—(1) Shape: Flat and nearly circular. (2) Color top side in winter when opening: between red 46B and 45A (color greatly intensifies with cool temperature), fading to between red 45B-C winter to darker than 42A in summer, under side red 45BC to 44A.(3) Number of tepals: From 4 to 30. (4) Size of tepals: Basal up to 25 mm.; interior 15 mm. (5) Flower size: Up to 5 cm. diameter.

(G) *Reproductive organs.*—(1) Stamens: None. (2) pistels: (a) stigma shape: Cork screw; color yellow. (b) Style color: Yellow to orange. (c) Ovaries: Three in number, size 5 mm.; exterior color, red.

Disease resistance:

Hilda appears to have above average resistance to powdery mildew when grown in the presence of mildew infected begonias.

I claim:

1. A new and distinct cultivar of begonia plant named Hilda, as described and illustrated, and particularly characterized by its deep red flower color; occasional pistillated flowers: ease of propagation; compact, upright growth habit, and by its floriferousness.

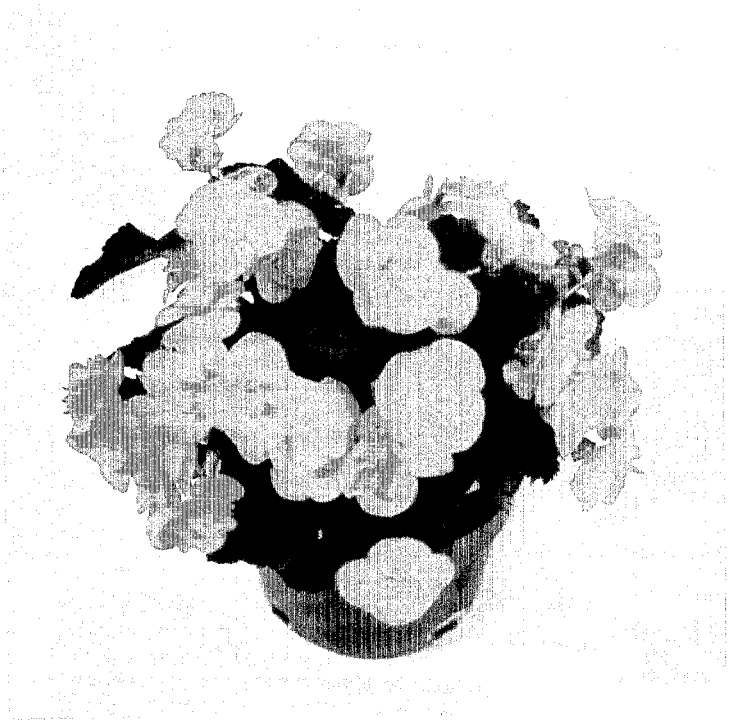

* * * * *